US008003829B2

(12) United States Patent
Heydrich et al.

(10) Patent No.: US 8,003,829 B2
(45) Date of Patent: Aug. 23, 2011

(54) RECOVERY OF PHENOL LIGANDS DURING THE PRODUCTION OF ISOPULEGOL

(75) Inventors: Gunnar Heydrich, Limburgerhof (DE); Gabriele Gralla, Mannheim (DE); Klaus Ebel, Lampertheim (DE); Marko Friedrich, Lorsch (DE)

(73) Assignee: BASF SE, Ludwigshafen (DE)

( * ) Notice: Subject to any disclaimer, the term of this patent is extended or adjusted under 35 U.S.C. 154(b) by 92 days.

(21) Appl. No.: 12/439,325

(22) PCT Filed: Aug. 31, 2007

(86) PCT No.: PCT/EP2007/059148
§ 371 (c)(1),
(2), (4) Date: Feb. 27, 2009

(87) PCT Pub. No.: WO2008/025851
PCT Pub. Date: Mar. 6, 2008

(65) Prior Publication Data
US 2010/0016642 A1 Jan. 21, 2010

(30) Foreign Application Priority Data

Sep. 1, 2006 (EP) .................... 06120012

(51) Int. Cl.
*C07C 35/08* (2006.01)
*C07C 35/12* (2006.01)
*C07C 29/80* (2006.01)
(52) U.S. Cl. .................... 568/828; 568/829; 568/830
(58) Field of Classification Search .................... None
See application file for complete search history.

(56) References Cited

U.S. PATENT DOCUMENTS

| 3,023,253 | A | 2/1962 | Bain et al. |
| 3,064,311 | A | 11/1962 | Bain et al. |
| 3,218,361 | A | 11/1965 | Webb |
| 3,739,035 | A | 6/1973 | Webb et al. |
| 5,663,460 | A | 9/1997 | Yamamoto et al. |
| 5,814,231 | A | 9/1998 | Borho et al. |
| 5,914,012 | A | 6/1999 | Kaibel et al. |
| 6,774,269 | B2 | 8/2004 | Iwata et al. |
| 2005/0169987 | A1 | 8/2005 | Korber |
| 2008/0139852 | A1 | 6/2008 | Bergner et al. |
| 2008/0167504 | A1 | 7/2008 | Friedrich et al. |
| 2008/0207957 | A1 | 8/2008 | Friedrich et al. |
| 2008/0214877 | A1 | 9/2008 | Rauls et al. |
| 2010/0010253 | A1 | 1/2010 | Heydrich et al. |
| 2010/0185024 | A1 | 7/2010 | Rauls et al. |

FOREIGN PATENT DOCUMENTS

| CH | 350461 A | 1/1961 |
| DE | 2530481 A1 | 1/1977 |
| DE | 2534558 A1 | 2/1977 |
| DE | 3302525 A1 | 7/1984 |
| DE | 19536827 A1 | 4/1997 |
| DE | 10224087 A1 | 12/2003 |
| EP | 0804951 A2 | 11/1997 |
| EP | 1053974 A1 | 11/2000 |
| EP | 1225163 A2 | 7/2002 |
| FR | 1374732 | 10/1964 |
| JP | 2004121903 A | 4/2004 |
| WO | WO-03/083028 A2 | 10/2003 |
| WO | WO-2006/056435 A1 | 6/2006 |
| WO | WO-2006/069659 A1 | 7/2006 |
| WO | WO-2006/092433 A1 | 9/2006 |

OTHER PUBLICATIONS

Wright, Fred, E., "The crystallization of menthol", J. Am. Chem. Soc., vol. 39, No. 8, pp. 1515-1525 (1917).
Kuhnert-Brandstaetter, et al. "Thermoanalytische Untersuchungen an Mentholen", Archiv der Pharmazie, vol. 307, No. 7, pp. 497-503 (1974).
Bernstein J., "Polymorphism in Molecular Crystals", Oxford, Clarendon Press, 2002, pp. 94-150 (2002).
Van't Land, C., M., "Industrial Crystallization of Melts", Marcel Dekker, pp. 61-63 (2005).
Arkenbout, G., F., "Melt Crystallization Technology", Technomic Publishing Company, Inc., Lancaster, Basel, pp. 229-232 (1995).
Wynn, Nicholas P., "Separate Organics by Melt Crystalization", Chemical Engineering Process, vol. 88, No. 3, (1992), pp. 52-60.

*Primary Examiner* — Brian J Davis
(74) *Attorney, Agent, or Firm* — Connolly Bove Lodge & Hutz LLP

(57) ABSTRACT

The present invention relates to a method of working up an aluminum-containing reaction product from the production of isopulegol by cyclization of citronellal in the presence of complex compounds, comprising at least one ligand of the formula (I),

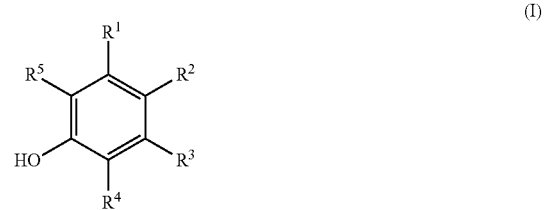

where $R^1$, $R^2$, $R^3$ are chosen from hydrogen, halogen, nitro, $C_1$-$C_8$-alkyl, $C_1$-$C_8$-alkoxy, di($C_1$-$C_4$-alkyl)amino and aryl; $R^4$, $R^5$ are chosen from halogen, nitro, $C_1$-$C_8$-alkyl, $C_1$-$C_8$-alkoxy, di($C_1$-$C_4$-alkyl)amino, aryl or heteroaryl;
in which a) the reaction product is subjected to distillative separation to obtain an isopulegol-enriched top product and an isopulegol-depleted bottom product and b) the ligand of the formula (I) is separated off from the bottom product.
Moreover, the invention relates to a method of producing isopulegol, and to a method of producing menthol.

22 Claims, No Drawings

RECOVERY OF PHENOL LIGANDS DURING THE PRODUCTION OF ISOPULEGOL

RELATED APPLICATIONS

This application is a national stage application (under 35 U.S.C. §371) of PCT/EP2007/059148, filed Aug. 31, 2007, which claims benefit of European Application No. 06120012.7, filed Sep. 1, 2006.

The present invention relates to a method of working up an aluminum-containing reaction product from the production of isopulegol by cyclization of citronellal in the presence of complex compounds, comprising at least one ligand of the formula (I).

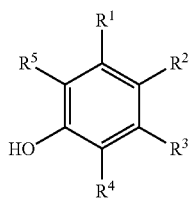
(I)

Moreover, the invention relates to a method of producing isopulegol, and to a method of producing menthol.

In terms of amount, menthol is the most important aroma chemical worldwide. The demand for menthol continues to be covered largely by isolation from natural sources. In addition, however, there are also synthetic routes to menthol, sometimes in racemic form, sometimes in the form of the natural enantiomer L-menthol.

An important intermediate for producing racemic such as optically active menthol is isopulegol, which is usually produced by a cyclizing oxo-ene reaction of citronellal in the presence of Lewis-acidic catalysts and is usually produced in the form of mixtures of the four diastereomers isopulegol, iso-isopulegol, neo-isopulegol and neoiso-isopulegol.

Suitable catalysts which have been described for carrying out the abovementioned cyclization of citronellal to isopulegol are both heterogeneous catalysts, such as $SiO_2$, $Al_2O_3$/$SiO_2$, $SiO_2/ZrO_2$, $SiO_2/TiO_2$ mixed catalysts, mordenites, faujasites, montmorillonites and zeolites—and also homogeneous catalysts, such as, for example, sulfonic acids or Lewis acids, such as, for example, $SnCl_4$, $ZnCl_2$ or $ZnBr_2$.

EP-A 1 225 163 describes the cyclization of citronellal to isopulegol in the presence of tris(2,6-diphenylphenol) aluminum catalysts. This method for cyclizing citronellal to isopulegol uses catalyst complexes which are expensive and can only be produced with complexity. After the described method, to be carried out in a homogeneous phase, the catalyst complex is hydrolyzed when the reaction is complete. Possible recovery and reusability of the ligand liberated in the process is not described.

Accordingly, it was an object of the present invention to provide a method which, after cyclization of citronellal to isopulegol has taken place, permits the phenol ligands used to be recovered in high purity and with good yield. Furthermore, this method should be particularly suitable as a continuous method.

Surprisingly, it has now been found that the phenol ligands used can be recovered in high purity and with good yield after cyclization of citronellal by distillative separation of the reaction product to give an isopulegol-enriched top product and an isopulegol-depleted bottom product and then separating off the ligand of the formula (I) from the bottom product. Moreover, it has been found that by bringing the isopulegol-depleted bottom product into contact with an aqueous base to give an aluminum-containing aqueous phase and an organic phase comprising the majority of the ligands of the formula (I) it is possible to increase the purity of the ligand of the formula (I) obtained from the separation. In particular, it has been found that the reaction product from the cyclization of citronellal can be passed to the distillative separation without prior hydrolysis.

The present invention thus provides a method for working up an aluminum-containing reaction product from the production of isopulegol by cyclizing citronellal, comprising
i) isopulegol,
ii) at least one ligand of the formula (I),

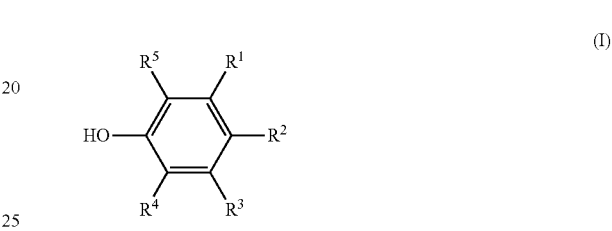
(I)

where
$R^1$, $R^2$, $R^3$ are in each case independently of one another chosen from hydrogen, halogen, nitro, $C_1$-$C_8$-alkyl, $C_1$-$C_8$-alkoxy, di($C_1$-$C_4$-alkyl)amino and optionally substituted or unsubstituted aryl, and
$R^4$, $R^5$ are in each case independently of one another chosen from halogen, nitro, $C_1$-$C_9$-alkyl, $C_1$-$C_8$-alkoxy, di($C_1$-$C_4$-alkyl)amino and optionally substituted or unsubstituted aryl or heteroaryl,
in free and/or complex-bound form,
in which
a) the reaction product is subjected to distillative separation to obtain an isopulegol-enriched top product and an isopulegol-depleted bottom product,
b) the ligands of the formula (I) are separated off from the bottom product.

In one preferred embodiment of the method according to the invention, the ligand of the formula (I) is separated off from the bottom product by crystallization.

One specific embodiment of tee present invention relates to a method as described above in which, after the distillative separation in step a) and before the separation in step b), the isopulegol-depleted bottom product is brought into close contact with an aqueous base to give an aluminum-containing aqueous phase and an organic phase comprising the majority of the ligands of the formula (I) (referred to below as step a.2).

The phenol ligands of the formula (I) obtained by the method according to the invention can usually be converted back to a reactive catalyst complex without further purification steps, with the corresponding aluminum compounds of the formulae (II) or (III), as defined below. No or no noteworthy decrease in the reactivity is generally established with the catalyst complexes recovered in this way.

Within the scope of the present invention the specified substituents can have the meanings given below by way of example:
$C_1$-$C_9$-alkyl such as, for example, methyl, ethyl, propyl, 1-methylethyl, butyl, 1-methylpropyl, 2-methylpropyl, 1,1-dimethylethyl, pentyl, cyclopentyl, 1-methylbutyl, 2-methylbutyl, 3-methylbutyl, 2,2-dimethylpropyl, 1-ethylpropyl, hexyl, cyclohexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, etc.;

$C_1$-$C_8$-alkoxy, such as, for example, methoxy, ethoxy, propoxy, 1-methylethoxy, butoxy, 1-methylpropoxy, 2-methylpropoxy and 1,1-dimethylethoxy, pentoxy, 1-methylbutoxy, 2-methylbutoxy, 3-methoxybutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy, heptyloxy, octyloxy, etc.;

Within the scope of the present invention, the term "halogen" is fluorine, chlorine, bromine and iodine, preferably fluorine and chlorine.

The radicals $R^1$, $R^2$ and $R^3$ have, for example, independently of one another the following meanings: hydrogen; halogen such as, for example, fluorine, chlorine, bromine or iodine; $C_1$-$C_9$-alkyl such as methyl, ethyl, propyl, isopropyl, n-butyl, isobutyl, sec-butyl, tert-butyl, pentyl, hexyl, heptyl, octyl; $C_1$-$C_8$-alkoxy, such as methoxy, ethoxy, propoxy, isopropoxy, butoxy, isobutoxy, sec-butoxy, tert-butoxy, pentoxy, hexoxy, heptoxy, octoxy; phenyl substituted, for example, by $C_1$-$C_4$-alkyl (e.g. methyl, ethyl, propyl, isopropyl, n-butyl, isobutyl, sec-butyl, tert-butyl), $C_1$-$C_4$-alkoxy (e.g. methoxy, ethoxy, propoxy, isopropoxy, butoxy, isobutoxy, sec-butoxy, tert-butoxy), halogen (e.g. fluorine, chlorine, bromine or iodine) and the like; naphthyl substituted by 1 to 7 substituents, such as, for example, $C_1$-$C_4$-allyl (e.g. methyl, ethyl, propyl, isopropyl, n-butyl, isobutyl, sec-butyl, tert-butyl), $C_1$-$C_4$-alkoxy (e.g. methoxy, ethoxy, propoxy, isopropoxy, butoxy, isobutoxy, sec-butoxy, tert-butoxy), halogen (e.g. fluorine, chlorine, bromine or iodine) and the like; di($C_1$-$C_4$-alkyl)amino such as, for example, dimethylamino, diethylamino, dipropylamino, diisopropylamino, dibutylamino; and nitro.

The radicals $R^4$ and $R^5$ can, independently of one another, have the meanings given above for $R^1$, $R^2$ and $R^3$ with the exception of hydrogen. Furthermore, $R^4$ and $R^5$ can, independently of one another, be heteroaryl, in particular furyl, thienyl, pyranyl, benzofuryl, isobenzofuryl, benzothienyl, indolyl, isoindolyl, carbazolyl, pyridyl, quinolyl, isoquinolyl or pyrazyl. The heteroaryls can in each case carry one or more of the substituents given above for phenyl.

Within the scope of the present invention, the term "ligand in free form" comprises both the free form of the ligand and all conceivable forms which can be converted into the free form under the process conditions. Examples thereof which may be mentioned are alkoxides of the ligand, which can be converted to the free form of the ligand by basic hydrolysis.

Within the scope of the present invention, the expression "aqueous base" generally comprises aqueous solutions whose pH is greater than 7. In particular, these are aqueous solutions of alkali metal and alkaline earth metal hydroxides, specifically aqueous solutions of KOH and NaOH.

Within the scope of the present invention, the expression "aluminum-containing reaction product" is a reaction product which comprises at least one compound which comprises aluminum in ionic, covalent or complex-bound form. These are compounds of aluminum as result under the conditions of the method according to the invention from the compounds of the formula $(R^{14})_{3-p}AlH_p$ (II) or $MAlH_4$ (III), as defined below, used in the cyclization of citronellal.

Within the scope of the present invention, the expression "majority" should be understood as meaning a percentage fraction of the total amount of a compound present which is greater than 50%, preferably greater than 80% and particularly preferably greater than 90%.

Surprisingly, it has been found that isopulegol can be distilled off in high purities from the aluminum-containing reaction products of the cyclization of citronellal without prior hydrolysis of the phenoxy-aluminum compounds used in each case as catalyst (if appropriate, following distillative removal of a solvent used and/or additionally used auxiliaries). As a rule, during the process, no recognizable undesired or troublesome by-products form in the distillation bottom. In one specific embodiment, a suitable, inert, higher-boiling solvent is added before or during the distillative separation in step a). This then gives, in the distillation bottom, a solution of the ligand of the formula (I) in the heated higher-boiling solvent used in each case.

One preferred embodiment of the present invention therefore relates to a method of working up an aluminum-containing reaction product from the cyclization of isopulegol in which the reaction product is subjected to distillative separation in step a) without prior hydrolysis.

Step a):

In step a) of the method according to the invention, the reaction product from the production of isopulegol by cyclization of citronellal is subjected to distillative separation to give an isopulegol-enriched top product and an isopulegol-depleted bottom product.

In a specific embodiment, step a) uses a solvent with a higher boiling point than that of the isopulegol. In this way, undesired thermal stressing of the bottom contents can be avoided. In particular, the ligands of the formula (I) present therein are not in a form free from solvent while separating off the isopulegol. The higher-boiling solvent can be added to the reaction product before and/or during distillative separation. Preference is given to using a higher-boiling solvent whose boiling point under the conditions of the distillation is above the boiling point of the isopulegol. Preferably, the boiling point of the introduced solvent under the conditions of the distillation is at least 5° C., preferably at least 10° C. and in particular at least 20° C., above the boiling point of the isopulegol.

Preferred higher-boiling solvents which have such a boiling point are, for example, hydrocarbons, such as phenylcyclohexane, phenyltoluene, dibenzyltoluene, 1-methylnaphthalene and tridecane, 1-decanol, 1,2-propylene carbonate, ethers, such as diethylene glycol dibutyl ether, tetraethylene glycol dimethyl ether and dibenzyl ether, and technical-grade mixtures of these solvents. Particular preference is given to mixtures which comprise phenylcyclohexane as main constituent.

When using at least one higher-boiling solvent, the isopulegol-depleted bottom product in step a) obtained is an organic phase comprising the higher-boiling solvent, the majority of the ligands of the formula (I) and, if appropriate, at least one aluminum-containing compound.

Preferably, distillative separation of isopulegeol in step a) takes place at a bottom temperature of at most 250° C., preferably at most 150° C. and particularly preferably at most 100° C. To maintain these maximum temperatures, the distillation can, if desired, be carried out under a suitable vacuum. The lower bottom temperature is usually uncritical and is generally at least 0° C., preferably at least 20° C.

The pressure in step a) of the method according to the invention is, irrespective of the specific embodiment, generally in a range from 0.1 to 1500 mbar, preferably in a range from 1 to 500 mbar and particularly preferably in a range from 5 to 100 mbar.

Irrespective of the composition of the reaction product from the cyclization of citronellal and of the use of a higher-boiling solvent, distillative separation of the isopulegol can take place continuously or batchwise, preferably continuously. In one suitable procedure, the higher-boiling solvent is added to the reaction product from step α) before distillative separation and in the course of the distillation the amount of higher-boiling solvent present in the bottom is subsequently kept constant.

For the distillative separation in step a), the customary devices known to the person skilled in the art can be used (see e.g. Sattler, Thermische Trennverfahren [Thermal separation methods], 2nd Edition 1995, Weinheim, p. 135ff; Perry's Chemical Engineers Handbook, 7th Edition 1997, New York, Section 13). These include distillation columns which may be provided with packings, internals etc. The distillation columns used can comprise separation-effective internals, such as separation trays, e.g. perforated trays, bubble-cap trays or valve trays, arranged packings, e.g. sheet-metal or fabric packings, or random beds of packings. The number of plates required in the column(s) used and the reflex ratio are essentially governed by the purity requirements and the relative boiling position of the constituents in the reaction product from the production of isopulegol by cyclization of citronellal and of the higher-boiling solvent, where the person skilled in the art can ascertain the specific design and operating data by known methods. The distillative separation can, for example, take place in one or more distillation columns coupled together.

Likewise suitable for the distillative separation in step a) are customary evaporators, preferably evaporators with forced circulation, particularly preferably falling-film evaporators.

Depending on additional components which may, if appropriate, be present in the reaction product from the cyclization of citronellal, the composition of the top product obtained during distillative separation may make it necessary to subject said product, if appropriate, to a further work-up step.

In a specific embodiment of the method according to the invention for working up a reaction product from the production of isopulegol by cyclizing citronellal, the reaction product additionally comprises a lower-boiling solvent (iii).

Within the scope of the present invention, the expression "lower-boiling solvent (iii)" refers to the boiling point of the isopulegol. Of particular suitability here are those solvents or solvent mixtures which, under the conditions of the distillative separation, have a boiling point which is at least 5° C., preferably 10° C. and in particular 20° C. below that of the isopulegol under the respective conditions.

Within the scope of the present invention, preferred solvents with such a boiling point are inert organic solvents or mixtures thereof, such as, for example, aromatic solvents, e.g. toluene, ethylbenzene or xylene, halogenated solvents, e.g. dichloromethane, dichloroethane or chlorobenzene, aliphatic solvents, e.g. pentane, hexane or cyclohexane, ethers, e.g. tetrahydrofuran, diethyl ether, methyl tert-butyl ether, esters, e.g. ethyl acetate, or dimethylformamide (DMF), dimethyl sulfoxide (DMSO) and the like. Particular preference is given to toluene.

If the reaction product to be worked up comprises such a lower-boiling solvent, then this is removed at least partially from the reaction product in a suitable embodiment prior to the distillative separation of the isopulegol. The lower-boiling solvent is likewise preferably separated off by distillation. Depending on the boiling point of the lower-boiling solvent, the customary abovementioned distillation devices can be used.

In a further suitable embodiment, distillative separation of the reaction product in step a) takes place to give an isopulegol-enriched top product which at the same time comprises at least some, preferably the majority, of the lower-boiling solvent. In this case, the top product can be subjected to further separation, preferably likewise by distillation.

The separated-off lower-boiling solvent is advantageously returned to the cyclization of the citronellal by using it as solvent. In this way, the method according to the invention requires—apart from top-ups which are required as a result of unavoidable losses—just the single provision of an amount of the lower-boiling solvent.

In a specific embodiment of the method according to the invention for working up a reaction product from the production of isopulegol by cyclizing citronellal, the reaction product additionally comprises an auxiliary (iv).

Within the scope of the present invention, the term "auxiliary" (iv) refers to compounds which are added during the cyclization of citronellal in order to suppress undesired secondary reactions. Preferably, the auxiliaries (iv) are chosen from organic acids, carboxylic anhydrides, aldehydes, ketones and vinyl ethers.

Specifically, the auxiliaries (iv) are chosen from acids, preferably organic acids. By way of example, organic acids which may be mentioned are: acetic acid, propionic acid, benzoic acid, toluenesulfonic acid, methanesulfonic acid, preferably acetic acid.

In a further specific embodiment of the present invention, the auxiliaries (iv) are chosen from carboxylic anhydrides, aldehydes, ketones and vinyl ethers.

The auxiliaries (iv) of said classes of substance can in each case be present individually or in the form of mixtures in the reaction product to be worked up. Preferred mixtures are those which consist of compounds of one class of substance. The reaction product particularly preferably comprises a single auxiliary.

Preferably, the auxiliaries (iv) present in the reaction product from the cyclization of citronellal are likewise at least partially removed and as far as possible returned to the cyclization of citronellal.

If the auxiliaries (iv) under the conditions of the distillation have a boiling point which is below or only slightly, i.e. less than 30° C., above the boiling point of the isopulegol, these can be largely recovered from the fully reacted mixture by distillation to the extent to which they were not, if appropriate, themselves reacted. Depending on the boiling point of the auxiliary, the customary abovementioned distillation devices can be used.

If the auxiliaries (iv) have a boiling point under the conditions of the distillation which is significantly above, i.e. at least 30° C., above the boiling point of the isopulegol, these remain in the bottom product and are, if appropriate, removed in step b) of the method according to the invention if their physical properties allow this.

In a further suitable embodiment, distillative separation of the reaction product in step a) takes place to give an isopulegol-enriched top product which at the same time comprises at least some, preferably the majority, of the auxiliary (iv). If appropriate, this main product can comprise a lower-boiling solvent, as explained above. In this case, the top product can be subjected to further separation, preferably likewise by distillation. The separated-off auxiliary (iv) is, if appropriate together with the lower-boiling solvent, advantageously returned to the cyclization of the citronellal, where it is used, for example, for suppressing undesired secondary reactions. In this way, the method according to the invention requires—apart from top-ups which are required as a result of unavoidable losses—just a single provision of an amount of the auxiliary (iv).

The separating off of isopulegol, the introduction of the higher-boiling solvent and, if appropriate, the separating off of low-boiling components, i.e. the separating off of any solvents present and volatile auxiliaries from the cyclization of citronellal, can be combined in various ways:

In one suitable embodiment, a so-called dividing wall column is used for the distillation, i.e. feed point and a side take-off are located on opposite sides of a dividing wall which extends along a section of the longitudinal expansion of the column. Such distillation columns which comprise a dividing wall are known per se to the person skilled in the art. If side take-off and feed are in the region of the dividing wall, a connection analogous to a Brugma or Petlyuk connection arises. Such distillations using dividing wall columns are described in DE-A-33 02 525 and EP-A-0 804 951, to the entire scope of which reference is hereby made. In this case, a fraction enriched with low-boiling components can be removed as top product, and a stream comprising the majority of isopulegol can be removed as side take-off, for example. The higher-boiling solvent is introduced below the feed point, preferably into the bottom of the column or just above the bottom. A solution of the majority of the ligand of the formula (I) in the higher-boiling solvent is produced as bottom product.

In an alternative embodiment, coupled columns are used for the distillation. This embodiment may be advantageous if the reaction product of the cyclization of citronellal comprises a solvent and/or a volatile auxiliary, as explained in more detail below.

In this case, mixtures of isopulegol and lower- or slightly higher-boiling solvents and/or auxiliary (iv) can form the top product of the first column and in the second column be subjected to separation to give a stream comprising at least the majority of the isopulegol and an isopulegol-depleted stream comprising the lower-boiling solvents and/or auxiliaries of the cyclization.

Streams which can comprise lower-boiling solvents (iii) and auxiliary (iv) of the cyclization can usually be returned to the cyclization without further separation.

The ligands of the formula (I) are produced, if appropriate in the form of their complexes or other derivatives, as bottom product of the first column.

In one preferred embodiment of the present invention, the isopulegol-depleted bottom product obtained in step a) is brought into contact with an aqueous base before separating off the ligand of the formula (I) in step b).

Step a.2):

In step a.2) of the method according to the invention, the isopulegol-depleted bottom product is brought into close contact with an aqueous base to give an aluminum-containing aqueous phase and an organic phase comprising the majority of the ligands of the formula (I). Preferred aqueous bases are given above.

Besides the ligand of the formula (I) in free or complex-bound form, the isopulegol-depleted bottom product obtained in step a) can comprise at least one further difficultly volatile component. These include, for example, higher-boiling solvents added in step a), the reaction products of the aluminum-containing compounds used for the cyclization of citronellal to isopulegol, and, if appropriate, auxiliaries (iv) not separated off in step a). Since aluminum-containing components and/or the auxiliaries (iv) accumulate particularly in the case of a continuous method and have an adverse effect especially on the yield and purity of the separation step b), it is advantageous to remove these compounds as completely as possible. This applies specifically to the aluminum-containing compounds.

The bringing into contact in step a.2) preferably takes place by extraction. The number of extraction stages is preferably in a range from 1 to 20 stages.

The extractants used are the abovementioned aqueous bases. These expressions are therefore used synonymously within the scope of the present invention.

For the extraction, the isopulegol-depleted bottom product from step a) is brought into close contact with an aqueous base. Separation of the phases gives a phase comprising the majority of the ligand of the formula (I), and an aqueous phase enriched in aluminum-containing compounds. Subsequently, the aqueous phase is removed. The bringing into contact can take place continuously or batchwise.

For the batchwise procedure, the isopulegol-depleted bottom product from step a) and the aqueous extractant are brought into contact with mechanical agitation, e.g. by stirring, in a suitable vessel, the mixture is left to stand for phase separation and one of the phases is removed by expediently drawing off the phase with the higher density at the bottom of the vessel.

A plurality of batchwise separation operations can be carried out successively in a cascade-like manner, in which case the phase separated off from the aqueous phase and comprising the majority of the ligand of the formula (I) is in each case brought into contact with a fresh portion of the aqueous extractant and/or the aqueous extractant is passed countercurrently.

For the continuous extraction procedure, the aqueous extractant and the stream of isopulegol-depleted bottom product from step a) is introduced continuously into suitable apparatuses in a manner analogous to the batchwise variant. At the same time, a discharge of the phase comprising the majority of the ligand of the formula (I) and a discharge of the aqueous phase enriched in aluminum-containing compounds are continuously removed from the apparatus in which phase separation takes place.

The extraction takes place at least in one stage, e.g. in a mixer-separator combination. Suitable mixers are either dynamic or static mixers. Extraction in a plurality of stages takes place, for example, in a plurality of mixer-separators or extraction columns.

In one suitable embodiment, at least one coalescing device is used to improve phase separation. This is preferably chosen from coalescing filters, electrocoalescers and combinations thereof. When using mixer-separator devices for the extraction, the use of coalescing filters, such as candle filters or sand filters, has proven advantageous for improving phase separation. The filter can be installed here directly after the mixer (stirred container) and/or in the organic run-off from the separator. Also preferred for improving phase separation is the use of electrocoalescers. These have proven useful for separating off aqueous foreign phases of up to 5% by mass. The use of coalescing devices is also advantageously suitable in the method according to the invention for separating off finely dispersed aqueous phase from the organic discharge of an extraction column comprising the majority of the ligand of the formula (I).

In one suitable embodiment, the extraction of aluminum-containing components from the isopulegol-depleted bottom product from step a) takes place in at least one mixer-separator combination. The use of a further mixer-separator combination is particularly advantageous for subsequently reextracting and thus return to the process fractions of the ligand of the formula (I) or, if appropriate, of the higher-boiling solvent which, if appropriate, with the aluminum-containing compounds to be separated off, partially pass into the extractant.

Under certain circumstances, it may be advantageous to subject the organic phase comprising the majority of ligands of the formula (I) to a drying step before the separation in step b) or after the separation. Suitable drying methods are the customary ones known to the person skilled in the art, in particular the adsorption to dehydrating agents, e.g. using a zeolitic molecular sieve.

In an alternative embodiment of the method according to the invention, after bringing the isopulegol-depleted bottom product into contact with the aqueous base, the water is removed by distillation.

In order to prevent the ligand of the formula (I) from separating off prematurely, by precipitation or crystallization, at no point during step a.2) should the solubility product of the ligand in the organic phase be exceeded. This can be carried out through appropriate choice of the temperature and/or the amount and type of added solvents, if appropriate.

Consequently, in a preferred embodiment of the method according to the invention, a discharge of the heated bottom product from step a) is brought into close contact with a heated aqueous base.

Within the scope of the present invention, the expression "heated" refers to a temperature above room temperature and below the respective boiling point temperatures of the aqueous or organic solutions under the reaction conditions in question. In particular, heated refers to a temperature in the range from 25 to 150° C., specifically in the range from 70° C. to 100° C.

Depending on the auxiliaries used, if appropriate, in the cyclization of citronellal, the isopulegol-depleted bottom product can, if appropriate, comprise further components not separated off in step a). These are preferably separated off in step a.2). In this case, the aqueous phase obtained can be subjected to a suitable separation process in order to recover these components, e.g. an auxiliary (iv).

In a further preferred embodiment of the method according to the invention, the ligand of the formula (I) is separated off in step b) directly from the isopulegol-depleted bottom product obtained in step a), i.e. without prior purification, by bringing it into contact with an aqueous base, as described under step a.2). For directly separating off the ligand from the bottom product obtained in step a), the same suitable and preferred embodiments apply as are listed below for the separation from the organic phase obtained in step a.2).

Step b):

In step b) of the method according to the invention, the ligand of the formula (I) is separated off from the organic phase comprising the majority of the ligand obtained in step a.2), where step b) can be carried out continuously or batchwise. Suitable embodiments of this step are, for example, crystallization or distillative removal of vaporizable constituents.

In one specific embodiment, the ligand of the formula (I) is separated off by crystallization.

For the crystallization of the ligand of the formula (I), the solubility product of the ligand of the formula (I) in the organic phase from step a.2) must firstly be exceeded. This can take place, for example, by a cooling process of the organic phase or by (partial) distillative separating off of the solvent. Methods for this purpose are known to the person skilled in the art. For the technical configuration of the method according to the invention, customary cooling crystallizers, evaporating crystallizers, vacuum crystallizers, crystallizing troughs or spray crystallizers, for example, are suitable.

In one preferred embodiment of the method according to the invention, crystallization takes place by cooling the organic phase from step a.2) of the method. In general, crystallization takes place at a temperature in the range from −50° C. to 100° C., preferably in the range from −20° C. to 5° C. and specifically in a range from 10° C. to 40° C.

This process can be accelerated by adding seed crystals.

The crystalline ligand of the formula (I) can be isolated from the solution, for example, by filtration, flotation, centrifugation or sieving.

The ligand of the formula (I) retained in this way can, if appropriate, be dried by suitable drying methods. Methods for this are known to the person skilled in the art. For example, for the technical configuration of the method, customary roller dryers, disk dryers, chamber dryers, fluidized-bed dryers or radiation dryers are suitable.

The organic phase depleted in ligand of the formula (I) can again be added to the process before or during step a).

In one suitable embodiment of the method according to the invention, crystallization takes place upon cooling to room temperature from a heated, saturated organic phase obtained in step a.2) or correspondingly from a heated bottom product obtained in step a).

In a preferred embodiment of the method for working up a reaction product from the production of isopulegol, the ligand of the formula (I) is chosen from 2,6-diarylphenol ligands of the formula (I.a)

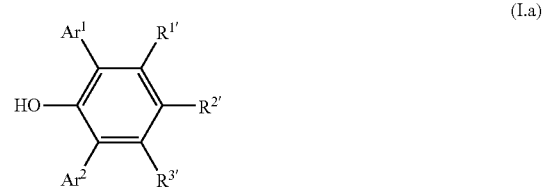

where
Ar$^1$ and Ar$^2$ are in each case independently of one another chosen from optionally substituted or unsubstituted aryl or heteroaryl and
R$^{1'}$, R$^{2'}$, R$^{3'}$ are in each case independently of one another chosen from hydrogen, halogen, nitro, C$_1$-C$_8$-alkyl, C$_1$-C$_8$-alkoxy, optionally substituted or unsubstituted aryl or di(C$_1$-C$_4$)alkylamino.

In one particularly preferred embodiment, the ligand of the formula (I) is 2,6-diphenylphenol.

The present invention further provides a method of producing isopulegol of the formula (IV)

comprising

α) the cyclization of citronellal of the formula (V)

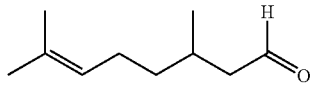
(V)

in the presence of a tris(phenoxy)aluminum catalyst which is obtainable by reacting a ligand of the formula (I), preferably a tris(biaiylphethoxy)aluminum catalyst, which is obtainable by reacting ligands of the formula (I.a), as defined above,
with an aluminum compound of the formula (II),

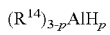
(II)

where
Al is aluminum,
$R^{14}$ is a branched or unbranched alkyl radical having 1 to 5 carbon atoms and
p is 0 or an integer from 1 to 3,
and/or
with an aluminum compound of the formula (III),

(III)

where
Al is aluminum and
M is lithium, sodium or potassium,
β) the recovery of the ligand of the formula (I) after the reaction has taken place by
  a) subjecting the reaction product obtained in step a) to distillative separation to obtain an isopulegol-enriched top product and an isopulegol-depleted bottom product,
  b) separating off the ligand of the formula (I) from the bottom product.

In a specific embodiment of the method according to the invention for producing isopulegol, the ligand of the formula (I) is separated off by crystallization.

The catalysts used in the method according to the invention and their preparation are described, for example, in EP-A 1 225 163, to which reference is hereby made in this regard. Usually, such catalysts are obtained by reacting the corresponding 2,6-disubstituted phenol ligands with suitable aluminum compounds, for example trimethylaluminum, triethylaluminum or diisobutylaluminum hydride.

A preferred embodiment of the above described method according to the invention for producing isopulegol of the formula (IV) comprises the recovery of the ligand of the formula (J) after reaction has taken place,
by, in step β),
  a) subjecting the reaction product obtained in step α) to distillative separation to obtain an isopulegol-enriched top product and an isopulegol-depleted bottom product, in addition
  a.2) bringing the isopulegol-depleted bottom product into close contact with an aqueous base to give an aluminium-containing aqueous phase and an organic phase comprising the majority of the ligands of the formula (I) and finally
  b) separating off the ligand of the formula (I) from the organic phase.

With regard to the preferred embodiments of the method according to the invention for working up a reaction product from the production of isopulegol by cyclization of citronellal, and with regard to the preferred ligands of the formula (I), reference is made to the above-mentioned preferred embodiments in their entirety.

The phenoxy-aluminum compounds used according to the invention as catalyst are obtained, for example, by reacting the abovedescribed ligands of the formulae (I) or (I.a) with an aluminum compound of the formula (HI)

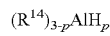
(II).

Here, 14 is a branched or unbranched alkyl radical having 1 to 5 carbon atoms, such as, for example, methyl, ethyl, propyl, isopropyl, butyl, isobutyl, pentyl, isopentyl or neopentyl. The index p is 0 or an integer from 1 to 3. Preferably, the index p is 1 or 0, particularly preferably 0. Preferred compounds of the formula (II) are, for example, trimethylaluminum, triethylaluminum, diisobutylaluminum hydride, particularly preferably trimethylaluminum and triethylaluminum.

Alternatively to this, the phenoxy-aluminum compounds used according to the invention can also be obtained by reacting the ligands of the formulae (I), preferably of the formula (I.a) with an aluminum compound of the formula (III)

(II), where M is lithium, sodium or potassium. Consequently, of suitability for producing the phenoxy-aluminum compounds used according to the invention by reacting the abovedescribed ligands of the formulae (I) or (I.a) are also lithium aluminum hydride, sodium aluminum hydride and potassium aluminum hydride, and mixtures thereof. Moreover, mixtures of the specified compounds of the formulae (II) and (III) are also suitable for producing phenoxy-aluminum compounds used according to the invention by reaction with the abovedescribed ligands of the formulae (I) or (I.a).

The reaction is advantageously carried out so that one of the abovedescribed ligands of the formulae (f) or (I.a) is brought into contact with a compound of the formula (II) or (III). The reaction is advantageously carried out in an inert organic solvent, such as, for example, toluene, cyclohexane, dichloromethane, xylene, ethylbenzene, chlorobenzene, tetrahydrofuran, diethyl ether, methyl tert-butyl ether, ethyl acetate, pentane, hexane, dichloroethane, dimethylformamide (DMF), dimethyl sulfoxide (DMSO) and the like, the use of predried or anhydrous solvents being regarded as particularly advantageous. The reaction is usually carried out at temperatures in the range from about −100° C. to about 100° C., preferably at about −50° C. to about 50° C., particularly preferably at about −30° C. to about 30° C.

During the production of the phenoxy-aluminum compounds according to the invention, the phenolic hydroxy groups of the ligands of the formulae (I) or (I.a) used react with the compound or compounds of the formulae (II) and (III). Theoretically, each aluminum atom can react with 1 to 3 phenolic hydroxy groups. On account of the steric properties or requirements of the ligands of the formulae (I) or (I a) used, this results in the formation of higher molecular weight structures such as linear structures or networks.

Here, the molar ratio of the ligands of the formulae (I) or (I.a) used to the compounds of the formula (II) and/or (III) used is advantageously chosen such that the amount of incompletely reacted compounds of the formulae (II) and/or (III) is as low as possible. Preferably, the specified ratio is chosen so that, after the ligands of the formulae (I) or (I.a) have been brought into contact with the compound or the compounds of the formulae (II) and (III), incompletely reacted compound of the formula (II) and/or (III) is no longer present. Taking into consideration the cost aspect, it is advisable to keep the excess of the ligands of the formulae (I) or (I.a) used low. Particular preference is given to using ligands of the formulae (I) or (I.a) and the compounds of the formulae (II) and/or (III) in a molar ratio of from about 4:1 to about 1:1, very particularly preferably from about 3:1 to about 1.5:1 and most preferably in the molar ratio of about 1.5:1.

Within the scope of a preferred embodiment of the present invention, the production of the phenoxy-aluminum compounds used according to the invention involves initially introducing, depending on the solubility, an about 0.001 to about 1 molar solution of the chosen ligand of the formula (I) or (I.a) into a suitable organic solvent, for example toluene, at a temperature of from about −10 to about 30° C., and adding an aluminum compound of the formula (II) and/or (III), preferably in the form of a solution, for example a solution of trimethyl- or triethylaluminum in toluene.

The reaction between the ligands of the formula (I) or (I.a) used and the aluminum compounds of the formulae (II) and/or (III) usually takes place rapidly and is mostly complete after about 10 min to about 2 h, often after about 1 h, depending on the reaction conditions chosen. When using more unreactive reactants, it may be advantageous to temporarily increase the temperature of the reaction mixture.

Depending on the reaction conditions chosen, in particular with regard to the solubility of the ligands of the formula (I) or (I.a) to be reacted and of the aluminum compound of the formula (II) and/or (III) in the chosen solvents, the concentrations and the reaction temperatures, the phenoxy-aluminum compounds used according to the invention are obtained in the form of a solid, a suspension or a solution in the solvent or solvent mixture used. The phenoxy-aluminum compounds used according to the invention obtained in this way can be further used in the form obtained in each case or are separated off and freed from the solvents used.

Isolation can take place here by methods which appear to be advantageous and are known to the person skilled in the art. Preferably, the isolation, storage and further treatment of the phenoxy-aluminum compounds used according to the invention are carried out with extensive exclusion of oxygen and moisture.

To carry out the method according to the invention for producing isopulegol, the procedure advantageously involves firstly preparing a solution of the phenoxy-aluminum compounds used according to the invention in a suitable solvent, as described above. The racemic or nonracemic citronellal to be cyclized is then added according to the invention to this solution. The citronellal can here be added as it is or in the form of a solution, advantageously in one of the abovementioned suitable solvents. Within the scope of a preferred embodiment of the method according to the invention, a solution of the chosen ligand of the formulae (I) or (I.a) in toluene is firstly prepared and then, advantageously with stirring, the chosen aluminum compound of the formula (II) and/or (III), preferably trimethylaluminum or triethylaluminum in toluenic solution, is added.

A suitable starting material for carrying out the cyclization method according to the invention is citronellal, which can be produced by any method. Preference is given to using citronellal which has a purity of about 90 to about 99.9% by weight, particularly preferably from about 95 to about 99.9% by weight.

The addition of the citronellal to be cyclized advantageously takes place at temperatures in the range from about −40° C. to about 40° C., preferably in the range from about −20° C. to about 20° C. For this, the prepared solution of the phenoxy-aluminum compound used according to the invention is advantageously cooled to a temperature in this range, e.g. to a temperature in the range from −10° C. to 10° C., and prechilled citronellal or a prechilled solution of citronellal is added.

The addition of the citronellal or of the solution thereof can be undertaken such that either the whole amount is added at once or it is added in portions or else continuously to the prepared catalyst solution. Suitable solvents in turn are the aboveinentioned solvents, in particular toluene. Preferably, the citronellal to be cyclized is used as it is, i.e. without the further addition of solvents. When using a solvent, the total amount of solvent (for catalyst production and for carrying out the cyclization reaction) is advantageously chosen so that the volume-based ratio of citronellal to be reacted to solvent is about 2:1 to about 1:20, preferably from about 1.5:1 to about 1:10.

The quantitative ratio between the citronellal to be reacted and the amount of phenoxy-aluminum compound used according to the invention used is determined by the amount of compounds of the formula (I) or (I.a) and of the formula (II) and/or (III) used for producing same, i.e. by the quantitative ratio of ligand used to aluminum compound of the formula (II) and/or (III) used.

According to the invention, the amount of citronellal to be reacted relative to the amount of aluminum compound of the formula (II) and/or (III) used is chosen such that the molar ratio is about 5:1 to about 1000:1, preferably about 10:1 to about 500:1, particularly preferably about 50:1 to about 200:1.

Irrespective of this, the ratio between ligand of the formula (I) or (I.a) used and the aluminum compound of the formula (II) and/or (III) used can be varied within the limits specified above for producing the phenoxy-aluminum compound according to the invention.

The cyclization of citronellal to isopulegol generally takes place rapidly, depending on the choice of reactants and reaction conditions, and is usually largely complete after about 0.5 to about 10 h, often after about 5 h. Reaction progress can be easily monitored by methods known per se to the person skilled in the art, for example by chromatographic, specifically gas chromatographic, methods or else HPLC methods.

Within the scope of a preferred embodiment of the method according to the invention, the cyclization of citronellal to isopulegol is carried out in the presence of an auxiliary (iv), for example an acid, preferably an organic acid. By way of example, organic acids which can be used advantageously are: acetic acid, propionic acid, benzoic acid, toluenesulfonic acid, methanesulfonic acid, preferably acetic acid. The specified acids are advantageously used in an amount of from about 0.5 to about 10% by weight, based on the amount of citronellal to be reacted. Advantageously, they are added to the reaction mixture together with the citronellal, e.g. in the form of a mixture.

In a particularly preferred embodiment, the method according to the invention for producing isopulegol by cyclizing citronellal is carried out in the presence of at least one auxiliary (iv) which is chosen from carboxylic anhydrides, aldehydes, ketones and vinyl ethers.

The auxiliaries (iv) of the specified classes of substance can in each case be used individually or in the form of mixtures with one another. In the case of mixtures, preference is given to using those which consist of compounds of one class of substance. Particular preference is given to using individual compounds. By using the specified compounds as described below, it is generally possible to largely suppress the formation of undesired by-products.

Within the scope of a preferred embodiment, the cyclization of citronellal is carried out in the presence of a carboxylic anhydride of the formula (VI)

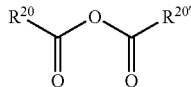

(VI)

where the radicals $R^{20}$ and $R^{20'}$ may be identical or different, preferably identical, and are chosen from branched or unbranched $C_1$-$C_{12}$-alkyl or $C_7$-$C_{12}$-aralkyl or $C_6$-$C_{10}$-aryl, where the specified radicals may in each case have one or more, generally 1 to about 3, identical or different substituents chosen from $OR^{10}$, $SR^{10}NR^8R^9$ and halogen and where $R^{20}$ and $R^{20'}$ can together also form a 5- to 8-membered ring which can have one or more ethylenic double bonds and one or more identical or different heteroatoms chosen from the group O, S and $NR^{11b}$ and where $R^8$, $R^9$, $R^{10}$, and $R^{11}$ are in each case independently of one another chosen from $C_1$-$C_6$-alkyl, $C_7$-$C_{12}$-aralkyl and optionally substituted or unsubstituted $C_6$-$C_{10}$-aryl.

Within the scope of a further preferred embodiment, the cyclization of citronellal is carried out in the presence of an aldehyde of the formula (VII)

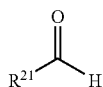

(VII)

where the radical $R^{21}$ is chosen from branched or unbranched $C_1$-$C_{12}$-alkyl or $C_7$-$C_{12}$-aralkyl or $C_6$-$C_{10}$-aryl, where the specified radicals can in each case have one or more, preferably 1 to 3, identical or different substituents chosen from $OR^{10}$, $SR^{10}NR^8R^9$ and halogen, where $R^8$, $R^9$ and $R^{10}$ are in each case independently of one another chosen from $C_1$-$C_6$-alkyl, $C_7$-$C_{12}$-aralkyl or optionally substituted or unsubstituted $C_6$-$C_{10}$-aryl.

Within the scope of a further preferred embodiment, cyclization of citronellal is carried out in the presence of a ketone of the formula (VIII)

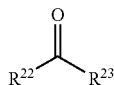

(VIII)

where the radicals $R^{22}$ and $R^{23}$ may in each case be identical or different and are chosen from branched or unbranched $C_1$-$C_{12}$-alkyl, $C_7$-$C_{12}$-aralkyl, $C_6$-$C_{10}$-aryl or $C_1$-$C_6$-alkoxycarbonyl, where the specified radicals can in each case have one or more, preferably 1 to 3 identical or different substituents chosen from $OR^{10}$, $SR^{10}NR^8R^9$ and halogen, and where $R^{22}$ and $R^{23}$ can together also form a 5- to 8-membered ring which can have one or more ethylenic double bonds and one or more identical or different heteroatoms chosen from O, S, $NR^{11}$ and where $R^8$, $R^9$, $R^{10}$ and $R^{11}$ are in each case independently of one another chosen from $C_1$-$C_6$-alkyl, $C_7$-$C_{12}$-aralkyl or optionally substituted or unsubstituted $C_6$-$C_{10}$-aryl.

As an alternative to the abovementioned carbonyl compounds, it is also possible to use vinyl ethers of the general formula (IX)

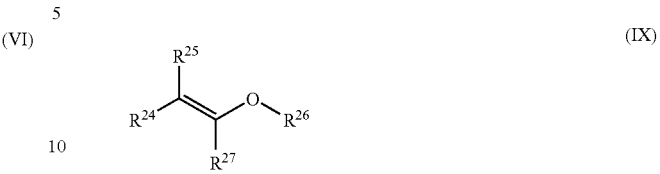

(IX)

within the scope of the method according to the invention, where the radicals $R^{24}$, $R^{25}$, $R^{26}$ and $R^{27}$, independently of one another, may in each case be identical or different and are chosen from branched or unbranched $C_1$-$C_{12}$-alkyl, $C_7$-$C_{12}$-aralkyl or $C_6$-$C_{10}$-aryl, where the specified radicals can in each case have one or more, preferably 1 to 3, identical or different substituents chosen from oxo, $OR^{10}$, $SR^{10}NR^8R^9$ and halogen and where $R^{25}$ and $R^{26}$ can together also form a 5- to 8-membered ring which can have one or more ethylenic double bonds and one or more, usually 1 or 2, identical or different heteroatoms chosen from O, S, $NR^{11}$ and where $R^8$, $R^9$, $R^{10}$ and $R^{11}$ are in each case independently of one another chosen from $C_1$-$C_6$-alkyl, $C_7$-$C_{12}$-aralkyl or optionally substituted or unsubstituted $C_6$-$C_{10}$-aryl.

Here, the following meanings may be given by way of example for the specified radicals $R^7$ to $R^{11}$: $C_1$-$C_6$-alkyl, such as, for example, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl; $C_7$-$C_{12}$-aralkyl, such as, for example, benzyl, 1-phenylethyl, 2-phenylethyl; $C_6$-$C_{10}$-aryl, such as phenyl or naphthyl.

Within the scope of a preferred embodiment of the method according to the invention, the cyclization of citronellal is carried out in the presence of a carboxylic anhydride of the formula (VI), where the radicals $R^{20}$ and $R^{20'}$ are identical and are chosen from branched or unbranched $C_1$-$C_{12}$-alkyl, $C_7$-$C_{12}$-aralkyl or $C_6$-$C_{10}$-aryl, and where $R^{20}$ and $R^{20'}$ can together also form a 5- to 8-membered ring which can have one or more ethylenic double bonds and one or more identical or different heteroatoms chosen from O, S, $NR^{11}$, in which $R^{11}$ can have one of the meanings given above.

Particular preference is given to using those carboxylic anhydrides in which the radicals $R^{20}$ and $R^{20'}$ are identical and are chosen from branched or unbranched $C_1$-$C_{12}$-alkyl or $C_6$-$C_{10}$-aryl. By way of example, carboxylic anhydrides to be used particularly preferably according to the invention are: acetic anhydride, propionic anhydride, pivalic anhydride and benzoic anhydride.

Aldehydes of the formula (VII) which can likewise be used preferably according to the invention are, by way of example, acetaldehyde, propionaldehyde and chloral (trichloroacetaldehyde).

If, within die scope of a further preferred embodiment, the cyclization of citronellal is carried out in the presence of a ketone of the formula (VIII), it is advantageous to use those with an activated, i.e. electron-deficient, carbonyl function. By way of example, mention may be made of the following ketones which are suitable to a particular degree for use within the scope of the method according to the invention: 1,1,1-trifluoroacetone, 1,1,1-trifluoroacetophenone, hexafluoroacetone, methyl pyruvate and ethyl pyruvate.

Vinyl ethers of the formula (IX) which can likewise be used with preference according to the invention are, for example: methyl vinyl ether, ethyl vinyl ether, isobutyl vinyl ether and 3,4-dihydro-2H-pyran.

The specified classes of compound can be used equally with good success within the scope of 50 this preferred embodiment of the method according to the invention. With regard to practical aspects such as, for example, a higher reaction rate, the use of aldehydes and/or electron-deficient ketones has proven to be advantageous.

The amount of carboxylic anhydride, aldehyde, ketone and/or vinyl ether to be used according to the invention can be varied within wide limits and is governed by the type of substance used and the degree of purity or the presence of impurities which are as yet not more precisely identified. Usually, the specified compounds and mixtures thereof are used in an amount of from about 0.01 mol % to about 5 mol %, preferably from about 0.1 mol % to about 2 mol %, based on the amount of citronellal used.

The type and manner of the procedure, for example the configuration of reactors or the order in which individual reactants are added, are not subject to particular requirements provided a procedure with extensive exclusion of oxygen and water is ensured.

To carry out the method according to the invention within the scope of this preferred embodiment, the procedure advantageously involves firstly providing a solution of the phenoxy-aluminum compound to be used according to the invention in a suitable solvent as described above. Then, according to the invention, a mixture of the racemic or nonracemic citronellal to be cyclized with the chosen carboxylic anhydride, the aldehyde, the activated ketone and/or the vinyl ether is preferably added to this solution. Alternatively thereto, it is possible, for example, to also admix the solution of the phenoxy-aluminum compound to be used according to the invention firstly with the carboxylic anhydride, of appropriate chosen in each case, the aldehyde, the ketone and/or the vinyl ether, and to afterwards add the citronellal to be cyclized.

It has proven to be advantageous to meter in the citronellal or the mixture of citronellal with the chosen compound to the catalyst solution or to the reaction mixture within a period of from about 30 min to about 6 h, preferably within about 2 h to about 4 h. The citronellal can here be added as such or in the form of a solution, advantageously in one of the above-mentioned suitable solvents. Within the scope of an again preferred embodiment of the method according to the invention, a solution of the chosen ligand of the formulae (I) or (I.a) in toluene is firstly provided, and then the chosen aluminum compound of the formula (II) and/or (III), preferably trimethylaluminum or triethylaluminum in toluenic solution is added, expediently with stirring.

The addition of the citronellal to be cyclized or the mixture of citronellal with the chosen carboxylic anhydride, aldehyde, activated ketone and/or the vinyl ether takes place within the scope of this embodiment advantageously at temperatures in the range from about −40° C. to about 40° C., preferably in the range from about −20° C. to about 20° C. For this, the prepared solution or suspension of the phenoxy-aluminum compound according to the invention is advantageously cooled to a temperature within this range, e.g. to a temperature in the range from −10° C. to 10° C., and the other reactants are added in precooled form.

The addition of the mixture of citronellal and the chosen further compound can be undertaken so that either the total amount of citronellal is added in one go or it is added in portions or continuously to the prepared catalyst solution. Suitable solvents are in turn preferably the abovementioned solvents, in particular toluene. Preference is given to using the citronellal to be cyclized in the form of a mixture with the chosen carboxylic anhydride, aldehyde, activated ketone and/or vinyl ether without the further addition of solvents. When using a solvent, the total amount of solvent is advantageously chosen so that the volume-based ratio of citronellal to be reacted to the solvent is about 1:1 to about 1:20, preferably from about 1:1 to about 1:10.

It has been found that some of the catalyst complex is usually deactivated during the reaction. This is attributed, inter alia, to ligand exchange processes between the ligands of the formula (I) used in each case of the phenoxy-aluminum compounds used and the isopulegol which forms as a result of cyclization. The deactivated form of the catalyst is, depending on the choice of solvent used, usually soluble in the reaction mixture.

Alternatively, the amount of catalyst used can be chosen so that the total catalyst complex used is deactivated in the course of or at the end of the cyclization reaction according to the invention. Here, it is advantageously notable that in this case, on account of the abovedescribed ligand exchange processes, the ligand of the formula (I) used in each case is released without separate hydrolysis being carried out.

As already mentioned, the method according to the invention is equally suitable for cyclizing racemic and nonracemic, i.e. optically active, citronellal to give racemic and nonracemic isopulegol.

In a preferred embodiment, the method according to the invention thus serves for producing optically active isopulegol of the formula (IV.a)

(IV.a)

by cyclization of optically active citronellal of the formula (V.a)

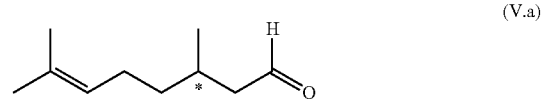

(V.a)

where (*) in each case refers to an asymmetric carbon atom.

The method according to the invention serves in particular for producing L-(−)-isopulegol by cyclization of D-(+)-citronellal.

The racemic or nonracemic isopulegol produced in this way is a valuable intermediate for producing racemic or nonracemic menthol, one of the most significant fragrances or aromas worldwide. Menthol can be obtained from isopulegol by methods of hydrogenation known per se to the person skilled in the art, specifically catalytic hydrogenation over suitable transition metal catalysts, as described, for example, in Pickard et al., J. Chem. Soc. 1920, 1253; Ohloff et al., Chem. Ber. 1962, 95, 1400; Pavia et al., Bull. Soc. Chim. Fr. 1981, 24, Otsuka et al., Synthesis 1991, 665 or in EP 1 053 974 A. Here, if the chosen reaction conditions are suitable, the relative or absolute configuration of the isopulegol used is largely retained, and in many cases is completely retained.

The present invention therefore further provides a method of producing menthol comprising the steps:
A) production of isopulegol of the formula (IV) by a method according to the invention
B) hydrogenation of the ethylenic double bond of the isopulegol obtained in this way.

In a preferred embodiment, this method serves for producing optically active menthol, specifically for producing L-(−)-menthol from optically active L-(−)-isopulegol.

With regard to the preferred embodiments of the method according to the invention for producing isopulegol, reference is made to the abovementioned preferences in their entirety.

The examples below serve to illustrate the present invention without having any limiting character.

Gas chromatographic analyses were carried out according to the following method:
50 m DP-WAX, ID.: 0.32 mm, FD.: 1.2 ym; 80° C., 36-230° C., 15° C./min to 250° C.; $t_R$ (phenylcyclohexane): 16.5; $t_R$ (isopulegol): 13.7; $t_R$ (citronellal): 10.2.

The following HPLC method was used: CC250/4 Nucleodur C18 Gravity, 5 ym; C: water—0.05% $H_3PO_4$; D: acetonitrile 20:80; exit: 93 bar, 25° C.; $t_R$ (phenylcyclo-hexane): 10.6; $t_R$ (isopulegol): 3.3; $t_R$ (diphenylphenol): 4.8. Concentrations of the reaction products obtained were determined analytically by GC and HPLC.

EXAMPLE 1

Method of Working Up 2,6-diphenylphenol 2,6-Diphenylphenol (25 g, 101.5 mmol) in anhydrous toluene (731 ml) was initially introduced into a heat-dried flask. At room temperature, a solution of triethylaluminum in toluene (0.66 M, 18.2 ml, 33.8 mmol) was added to the clear solution. The solution was stirred for 1 h at 25° C. The resulting catalyst solution was cooled to 0° C. and, over a period of 3 h, admixed with a mixture of citronellal (258.7 g, 1.68 mol) and methyl pyruvate (2.07 g, 0.02 mol). When addition was complete, the reaction mixture was after-stirred for 3 h at 006 and for a further 12 h at room temperature. The solvent toluene was removed by distillation via a column (diameter: 30 mm, packing 280 mm, packing 5 mm metal rings, 100 mbar, top temperature 43-46° C., bottom temperature 48-85° C.) and the isopulegol obtained as distillation residue was distilled off under reduced pressure (6 mbar, top temperature 55° C., bottom temperature 75° C.). The first fraction comprised isopulegol (38.6 g) in a purity of 98.4%. The isopulegol remaining in the distillation bottom was distilled off with addition of phenylcyclohexane (52 g) under reduced pressure (6 mbar, top temperature 53-54° C., bottom temperature 77-88° C.). The second fraction produced isopulegol (224 g) in a purity of 90.1%. The total yield of isolated isopulegol was 93%. The 2,6-diphenylphenol used as ligand during the reaction crystallized out from the oily bottom product after cooling to 25° C. over the course of 12 h. The suspension was filtered off by means of a glass suction filter and then the filter cake was dried at a temperature of 95° C. and 3 mbar. 2,6-diphenylphenol was obtained as a crystalline solid (16.7 g) with a yield of 67%. This solid, the mother liquor of the crystallization and the bottom product from the distillative separation were analyzed by means of liquid chromatography. The results are shown in table 1:

TABLE 1

|  | Isopulegol HPLC % by wt. (area %) | 2,6-Diphenylphenol HPLC % by wt. (area %) | Phenylcyclohexane HPLC % by wt. (area %) |
|---|---|---|---|
| 2,6-Diphenylphenol |  | 99.0 |  |
| Distillation bottom (62.9 g) | 2.19 (0.6) | 42.6 (73.43) | 40.92 (21.95) |
| Mother liquor (32.5 g) | 2.73 (1.06) | 19.07 (48.0) | 56.02 (43.0) |

EXAMPLE 2

Method of Working Up 2,6-diphenylphenol (Comprising the Hydrolysis of the Bottom Product)

2,6-Diphenylphenol (25 g, 101.5 mmol) in anhydrous toluene (731 ml) was initially introduced into a heat-dried flask. At room temperature, a solution of triethylaluminum in toluene (0.66 M, 18.2 ml, 33.8 mmol) was added to the clear solution. The solution was stirred for 1 h at 25° C. The resulting catalyst solution was cooled to 0° C. and, over a period of 3 h, admixed with a mixture of citronellal (375 g, 2.43 mol) and methyl pyruvate (3.75 g, 0.04 mol). When addition was complete, the reaction mixture was after-stirred for 3 h at 0° C. and for a Angler 12 h at room temperature. The solvent toluene was removed by distillation via a column (diameter: 30 mm, packing 280 mm, packing 5 mm metal rings, 100 mbar, top temperature 43-46° C., bottom temperature 48-85° C.) and the isopulegol obtained as distillation residue was distilled off under reduced pressure (6 mbar, top temperature 55-62° C., bottom temperature 75-115° C.). The first fraction comprised isopulegol (341.9 g) in a purity of 98.4%. The isopulegol remaining in the distillation bottom was distilled off with addition of phenylcyclohexane (40.5 g) under reduced pressure (6 mbar, top temperature 72° C., bottom temperature 95-104° C.). The second fraction produced a mixture comprising 56.9% isopulegol (26.7 g) and 39.9% phenylcyclohexane. The total yield of isolated isopulegol was 95%.

Some of the bottom product of the distillative separation (26 g) was diluted with phenylcyclohexane (653 g) and hydrolyzed with a 2% strength aqueous NaOH solution (104 ml). The suspension was stirred for 20 minutes at room temperature. During this time, the aluminum present in the bottom product precipitated out as hydroxide. Following phase separation, the organic phase was dried over sodium sulfate and filtered. The phenylcyclohexane was removed by distillation (95° C.6, 3 mbar). 2,6-diphenylphenol was obtained as a white solid with a yield of 12.1 g.

This solid and the bottom product from the distillative separation were analyzed by means of liquid chromatography. The results are shown in table 2:

TABLE 2

| | Isopulegol HPLC % by wt. (area %) | 2,6-Diphenylphenol HPLC % by wt. (area %) | Phenylcyclohexane HPLC % by wt. (area %) |
|---|---|---|---|
| 2,6-Diphenylphenol (12.1 g) | | 99.0 | |
| Distillation bottom (26 g) | | 78.9 | 18.8 |

The invention claimed is:

1. A method for working up an aluminum-containing reaction product from the production of isopulegol by cyclizing citronellal, comprising
   i) isopulegol; and
   ii) at least one ligand of formula (I),

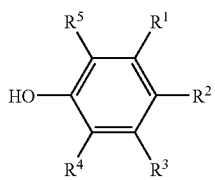

(I)

wherein
$R^1$, $R^2$, and $R^3$
   are, in each case independently of one another, hydrogen, halogen, nitro, $C_1$-$C_8$-alkyl, $C_1$-$C_8$-alkoxy, di($C_1$-$C_4$-alkyl)amino, or optionally substituted aryl; and
$R^4$ and $R^5$
   are, in each case independently of one another, halogen, nitro, $C_1$-$C_8$-alkyl, $C_1$-$C_8$-alkoxy, di($C_1$-$C_4$-alkyl)amino, or optionally substituted aryl or heteroaryl;
in free and/or complex-bound form;
said method comprising
   a) subjecting the reaction product to distillative separation to obtain an isopulegol-enriched top product and an isopulegol-depleted bottom product; and
   b) separating the ligands of formula (I) off from said isopulegol-depleted bottom product.

2. The method of claim 1, wherein said ligand of formula (I) is separated off from said isopulegol-depleted bottom product in b) by crystallization.

3. The method of claim 1,
wherein
   a) subjecting the reaction product to distillative separation to obtain an isopulegol-enriched top product and an isopulegol-depleted bottom product;
   a.2) bringing said isopulegol-depleted bottom product into close contact with an aqueous base to give an aluminium-containing aqueous phase and an organic phase comprising the majority of the ligands of formula (I); and
   b) separating off the ligands of formula (I) from said organic phase.

4. The method of claim 1, wherein said aluminum-containing reaction product from the production of isopulegol by cyclizing citronellal additionally comprises a lower-boiling solvent (iii).

5. The method of claim 1, wherein said aluminum-containing reaction product from the production of isopulegol by cyclizing citronellal additionally comprises an auxiliary (iv).

6. The method of claim 5, wherein said auxiliary (iv) is selected from the group consisting of organic acids, carboxylic anhydrides, aldehydes, ketones, and vinyl ethers.

7. The method of claim 1, wherein said aluminum-containing reaction product from the production of isopulegol by cyclizing citronellal is not hydrolyzed prior to step a).

8. The method of claim 1, wherein, prior to the distillative separation in a), any solvent present and/or auxiliaries from the cyclization are first separated off from said reaction product.

9. The method of claim 1, wherein, prior to and/or during the distillative separation in a), said reaction product is admixed with a solvent whose boiling point, under the distillation conditions, is at least 10° C. higher than the boiling point of isopulegol.

10. The method of claim 1, wherein at least one of a) and b) is operated continuously.

11. The method of claim 9, where the addition of the higher-boiling solvent takes place during a).

12. The method of claim 3, wherein a heated discharge of the bottom product from a) is brought into contact with a heated aqueous base and then the majority of the ligand is isolated from the organic phase by crystallization.

13. The method of claim 1, wherein the ligand of formula (I) is a diarylphenol ligand of formula (I.a)

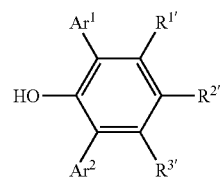

(I·a)

wherein
$Ar^1$ and $Ar^2$
   are, in each case independently of one another, optionally substituted aryl or heteroaryl.

14. A method of producing isopulegol of formula (IV):

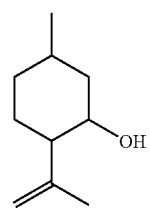

(IV)

comprising
α) cyclizing citronellal of formula (V):

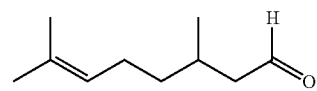

(V)

in the presence of a tris(phenyloxy)aluminum catalyst obtained by reacting a ligand of formula (I):

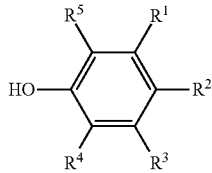

(I)

wherein
$R^1$, $R^2$, and $R^3$
are, in each case independently of one another, hydrogen, halogen, nitro, $C_1$-$C_8$-alkyl, $C_1$-$C_8$-alkoxy, di($C_1$-$C_4$-alkyl)amino, or optionally substituted aryl; and
$R^4$ and $R^5$
are, in each case independently of one another, halogen, nitro, $C_1$-$C_8$-alkyl, $C_1$-$C_8$-alkoxy, di($C_1$-$C_4$-alkyl) amino, or optionally substituted aryl or heteroaryl;
with an aluminum compound of formula (II):

$(R^{14})_{3-p}AlH_p$ (II)

wherein
Al is aluminum;
$R^{14}$ is a branched or unbranched alkyl radical having up to 5 carbon atoms; and
p is 0 or an integer from 1 to 3;
and/or
with an aluminum compound of the formula (III):

$MAlH_4$ (III)

wherein
Al is aluminum; and
M is lithium, sodium, or potassium; and
β) recovering the ligand of formula (I) after the reaction has taken place by
a) subjecting the reaction product obtained in a) to distillative separation to obtain an isopulegol-enriched top product and an isopulegol-depleted bottom product; and
b) separating off the ligand of formula (I) from said isopulegol-depleted bottom product.

15. The method of claim 14, wherein the ligand of formula (I) is separated off from said isopulegol-depleted bottom product in b) by crystallization.

16. The method of claim 14, comprising
β) recovering the ligand of formula (I) after the reaction has taken place by
a) subjecting the reaction product obtained in a) to distillative separation to obtain an isopulegol-enriched top product and an isopulegol-depleted bottom product;
a.2) bringing said isopulegol-depleted bottom product into close contact with an aqueous base to give an aluminum-containing aqueous phase and an organic phase comprising the majority of the ligands of formula (I); and
b) separating off the ligands of formula (I) from said organic phase.

17. The method of claim 14, where said aluminum compound of formula (II) is selected from the group consisting of trimethylaluminum and triethylaluminum.

18. The method of claim 14, wherein the isopulegol of formula (IV) produced is optically active isopulegol of formula (IV.a)

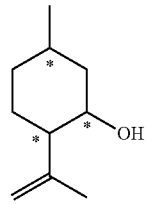

(IV.a)

and wherein the citronellal of formula (V) cyclized in a) is optically active citronellal of formula (V.a)

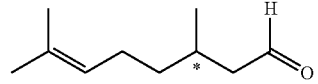

(V.a)

wherein (*), in each instance, indicates an asymmetric carbon atom.

19. The method of claim 18, wherein the optically active isopulegol of formula (IV.a) is L-(−)-ispulegol and the optically active citronellal of formula (V.a) is D-(+)-citronellal.

20. A method of producing menthol, comprising:
A) producing isopulegol of formula (IV) according to the method of claim 14; and
B) hydrogenating the ethylenic double bond of the isopulegol of formula (IV) obtained in A).

21. A method for producing optically active menthol, comprising:
A) producing optically active isopulegol of formula (IV.a) according to the method of claim 18; and
B) hydrogenating the ethylenic double bond of the optically active isopulegol of formula (IV.a) obtained in A).

22. A method for producing L-(−)-menthol; comprising:
A) producing L-(−)-isopulegol according to the method of claim 19; and
B) hydrogenating the ethylenic double bond of the L-(−)-isopulegol obtained in A).

* * * * *